(12) United States Patent
Pruitt et al.

(10) Patent No.: US 7,083,919 B2
(45) Date of Patent: Aug. 1, 2006

(54) HIGH THROUGHPUT ASSAY FOR IDENTIFICATION OF GENE EXPRESSION MODIFIERS

(75) Inventors: Steven C. Pruitt, Williamsville, NY (US); David G. Hangauer, East Amherst, NY (US); Carleton C. Stewart, Orchard Park, NY (US); Lawrence Mark Mielnicki, Buffalo, NY (US)

(73) Assignee: The Research Foundation of State University of New York, Amherst, NY (US)

(*) Notice: Subject to any disclaimer, the term of this patent is extended or adjusted under 35 U.S.C. 154(b) by 179 days.

(21) Appl. No.: 10/139,420

(22) Filed: May 6, 2002

(65) Prior Publication Data

US 2002/0164636 A1 Nov. 7, 2002

Related U.S. Application Data

(60) Provisional application No. 60/288,994, filed on May 4, 2001.

(51) Int. Cl.
*C12Q 1/68* (2006.01)
*C12Q 1/02* (2006.01)
*C12Q 15/63* (2006.01)

(52) U.S. Cl. .................. 435/6; 435/29; 435/320.1
(58) Field of Classification Search .............. 435/6, 435/320.1, 29; 425/7.1
See application file for complete search history.

(56) References Cited

U.S. PATENT DOCUMENTS

| | | | |
|---|---|---|---|
| 5,695,937 A | 12/1997 | Kinzler et al. | |
| 5,866,330 A | 2/1999 | Kinzler et al. | |
| 5,922,601 A | 7/1999 | Baetscher et al. | |
| 5,928,888 A | 7/1999 | Whitney | |
| 6,020,192 A * | 2/2000 | Muzyczka et al. | 435/320.1 |
| 6,080,576 A | 6/2000 | Zambrowicz et al. | |
| 6,207,371 B1 | 3/2001 | Zambrowicz et al. | |
| 6,214,563 B1 * | 4/2001 | Negulescu et al. | 435/7.1 |
| 6,303,327 B1 | 10/2001 | Von Melchner et al. | |
| 6,383,743 B1 | 5/2002 | Kinzler et al. | |
| 6,436,707 B1 | 8/2002 | Zambrowicz et al. | |
| 2003/0143597 A1 * | 7/2003 | Finney et al. | 435/6 |

FOREIGN PATENT DOCUMENTS

| | | |
|---|---|---|
| EP | 0 818 534 A1 | 1/1998 |
| WO | WO 98/13353 A | 4/1998 |
| WO | WO 99/43848 | 9/1999 |

OTHER PUBLICATIONS

Durick, et al. Hunting with Traps: Genome–Wide Strategies for Gene Discovery and Functional Analysis. Genome Research. 1999. 9:1019–1025.
Pruitt. Expression of *Pax–3–* and Neuroectoderm–Inducing Activities During Differentiation of P19 Embryonal Carcinoma Cells. Development. 1992. 116:573–583.
Pruitt, et al. Positive and Negative DNA Sequence Elements are Required to Establish the Pattern of *Pax3* Expression. Development. 1997. 124:617–626.
Skarnes, et al. A Gene Trap Approach in Mouse Embryonic Stem Cells: The *lacZ* Reporter is Activated by Splicing, Reflects Endogenous Gene Expression, and is Mutagenic in Mice. Genes & Development. 1992. 6:903–918.
Baghdoyan, et al., *Capture of Cytokine–Responsive Genes (NACA and RBM3) Using a Gene Trap Approach*, Blood (Jun. 15, 2000) vol. 95, No. 12, pp. 3750–3757.
Bronchain, et al., *A Gene Trap Approach in Xenopus*, Current Biology, (Oct. 11, 1999) vol. 9, No. 20, pp. 1195–1198.
Gogos, et al., *Selection for Retroviral Insertions into Regulated Genes*, Journal of Virology (Feb. 1997) vol. 71, No. 2, pp. 1644–1650.

* cited by examiner

*Primary Examiner*—Bennett Celsa
*Assistant Examiner*—Mark L. Shibuya
(74) *Attorney, Agent, or Firm*—Hodgson Russ LLP

(57) ABSTRACT

The present invention provides a method for screening of a large number of compounds for their ability to modulate the expression of genes. The method uses gene trap technology and comprises the steps of transfecting a population of cells with a gene-trap vector, sorting cells according to their level of fluorescence, distributing sorted cells into pools and expanding the pools to obtain a sufficient number of cells representing each trapped gene to permit distinction of the effect of a test compound over controls, exposing the cells to the test compounds and identifying compounds which alter the fluorescence distribution pattern of cells using FACS analysis.

17 Claims, 10 Drawing Sheets

POST 2ND SORT FRACTION ANALYSIS

1.5 SORT DROPS

Conventional Methodology

Forward-Scatter Compensation Process

US 7,083,919 B2

HIGH THROUGHPUT ASSAY FOR IDENTIFICATION OF GENE EXPRESSION MODIFIERS

This application claims priority of U.S. Provisional application Ser. No. 60/288,994 filed on May 4, 2001, the disclosure of which is incorporated herein by reference.

FIELD OF THE INVENTION

This invention relates generally to the field of drug screening and more particularly provides a method for high throughput multiplexed screening of test compounds for their effect on gene expression.

BACKGROUND OF THE INVENTION

Technologies for marking genes by the random integration of DNA sequences containing a detectable reporter (marker) are known and referred to as gene-trapping (Skarnes et al., 1992, Genes Dev., 6:903–18; Durick et al., 1999, Genome Res., 9:1019–1025; Pruitt et al., Development, 1997, 124:617–626). Gene-trap technologies provide vectors that typically do not contain a promoter. Instead, gene trap vectors provide specific sequences that generate fusion RNA transcripts when inserted into a gene. This makes gene trapping especially attractive for mammalian cells since these cells have complex genomic organization including large introns and small exons. The trapped gene can then be identified by mRNA sequence. Using these technologies it is possible to create libraries of cells in which the expression of the reporter gene provides measures of the activities of the genes (trapped genes) into which it is integrated Further, the genes that can be trapped represent the majority of genes within the cell.

Technologies are available for identification of trapped genes. In the gene-trap methods, identification of the trapped genes is based on the generation of fusion mRNA that contains the mRNA for the reporter protein. Subsequently, the gene in which the reporter gene has been inserted (the trapped gene) can be cloned by using standard techniques such as rapid amplification of cDNA (RACE).

For measurement of expression of the trapped genes, standard detecting techniques for the reporter gene have been used. For fluorescent reporters, such techniques include fluorescence activated cell sorting (FACS).

Libraries of trapped genes have been used to identify genes that respond to specific chemical compounds (Pruitt, 1992; Whitney, 1999, U.S. Pat. No. 5,928,888). Pruitt teaches inserting a β-galactosidase expression construct into a eukaryotic genome in a cell and contacting the cell with a chemical to detect changes in β-galactosidase activity. Whitney discloses inserting a beta lactamase expression construct into an eukaryotic genome in a cell and contacting the cell with a chemical to detect changes in the activity of beta lactamase. The prior art also provides for screening of a chemical compound for its ability to modulate gene expression, whereas the method of Whitney entails the use of FACS. However, there are limitations inherent to the prior art methods. First, although an individual chemical compound can be screened for an effect on multiple genes simultaneously, the method entails the preparative scale use of FACS to enrich for cells that respond to a given modulator over multiple rounds of enrichment. As a consequence, the method is prohibitively costly and time consuming to contemplate its use for high-throughput compound screens. Second, according to the method of Whitney, a library of cells containing trapped genes is divided into those that exhibit high levels of fluorescence and those that exhibit low levels of fluorescence, i.e. essentially on or off. FACS is used to enrich for cells that respond to a chemical compound by going from off to on, or on to off. Following the repeated rounds of enrichment discussed above, cells are recovered and the trapped genes are determined. Due to the inability of Whitney's method to resolve changes in gene expression less than that required to cause a cell to change from on to off, or off to on, qualitative changes in gene expression are not identified.

Accordingly, there is a need in the field of drug screening to develop methodologies whereby large number of compounds can be screened for their effects on the expression of genes and to develop methodologies whereby such effects can be determined by a quantitative measure.

BRIEF DESCRIPTION OF THE DRAWINGS

FIG. 2 is a representation of high velocity cell sorting of EGFP expressing cells. Cells were sorted using a cell stream velocity of 25 meters per second in a detection height of 30 microns. An initial plot of GFP fluorescence versus the forward scatter is shown in FIG. 2A.

SUMMARY OF THE INVENTION

Figure 1:
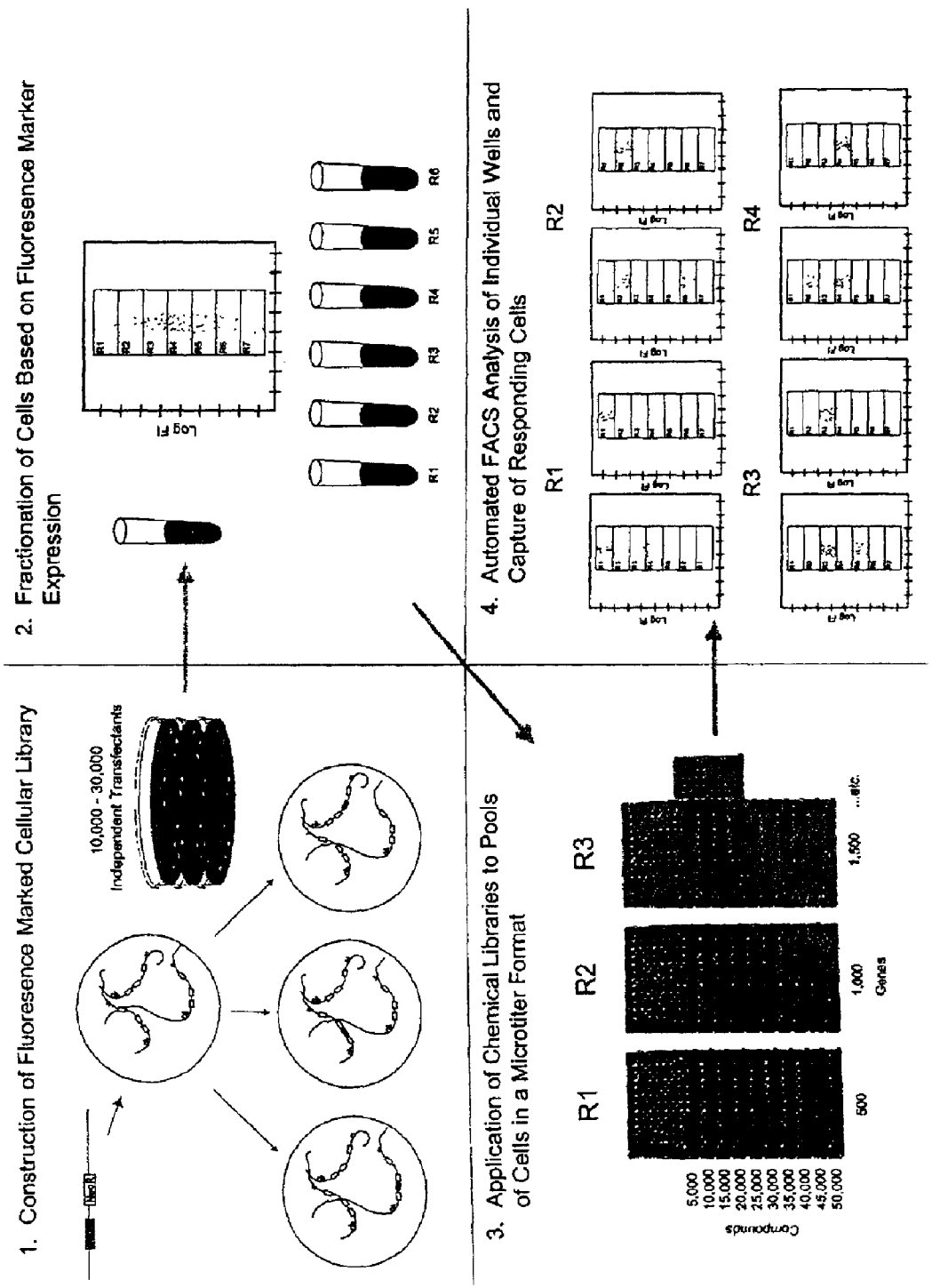
FIG. 1 is a schematic overview of the multiplex compound screen. Panel 1 illustrates construction of a fluorescence marked cellular library; Panel 2 illustrates fractionation of cells based on fluorescence marker expression; Panel 3 illustrated application of chemical libraries to pools of cells in a microtiter format; and Panel 4 illustrates automated FACS analysis of individual wells and capture of responding cells.

The present invention provides a method for screening of a large number of compounds for their ability to modulate the expression of genes. The method uses gene trap technology and comprises the steps of transfecting a population of cells with a gene-trap vector comprising a polynucleotide sequence encoding a fluorescent reporter protein, subjecting the population of cells to FACS analysis to sort cells into windows based upon the level of fluorescence, pooling cells from each window, expanding the pooled cells to obtain a sufficient number of copies of cells containing each trapped gene so as to permit detection of altered expression, exposing a certain number of cells from each pool to a plurality of chemicals, subjecting exposed cells to FACS analysis, identifying pools in which the fluorescence pattern has been altered over control cells, and correlating the altered pattern of fluorescence to specific chemicals.

The present invention further provides a method, wherein the trapped genes whose activity is altered upon exposure to test compounds are identified, cloned and sequenced.

In the present invention, methodologies are provided which improve the accuracy, stability and sensitivity of FACS screening thus allowing multiplex screening of chemical compounds. These methodologies are directed to reducing 1) the heterogeneity in the detection of fluorescence within a given cell during sorting that leads to inaccuracy in the determination of fluorescence; 2) heterogeneity in the detected fluorescence depending upon the stage of the cell cycle; and 3) cellular auto-fluorescence that reduces the sensitivity of fluorescence based assays. The accuracy is improved by increasing the residence time of each cell in the flow cytometer so as to reduce the heterogeneity in detection due to uneven illumination. The residence time is increased by reducing the cell stream velocity. The stability in improved by adjusting the parameters of sorting cells during FACS such that the variations due to cell cycling are minimized. The sensitivity is improved by suppressing the background by illuminating the sample with white light.

Thus, an object of the present invention is to overcome the limitation to the number of chemical compounds that can be screened for effects on populations of trapped genes in gene trap cellular libraries. Assessment of subsets of a gene trap cellular library for the effects of several chemical compounds simultaneously, i.e. multiplexing, allows for the enhancement in the number of genes x chemical compounds that can be assessed.

A further object of the present invention is to reduce the heterogeneity in fluorescence detection due to cell cycling.

A further object of the present invention is to reduce the heterogeneity in fluorescence detection due to high-speed sorting during FACS analysis.

A further objective is to suppress cellular auto-fluorescence. Suppression of auto-fluorescence increases the ability to measure low signal levels that result from genes expressed at minimal levels.

In one embodiment, a method is provided for generating pools from each group (window in the fluorescence distribution patterns from FACS analysis) of cells in which approximately 500 trapped genes are represented where expression from these genes is detected using the fluorescent protein reporter enhanced green fluorescent protein and where expression of this reporter from the trapped genes varies by less than a factor of approximately three (the range of fluorescence separating two neighboring windows in FACS) and where less than approximately 0.02%–0.03% of the cells deviate from these parameters.

In another embodiment, a population of cells is provided wherein cells maintain the desired properties for the assay period which may vary depending on the stability of the specific reporter gene used and whether up-regulated or down-regulated changes in gene expression are desired.

In another embodiment, an assay is provided in which approximately 29,800 chemical compound interactions with specific genes were assessed through the application of approximately 2,000 chemical compounds, in groups of 10, to microtitre wells containing pools of approximately 5,000–10,000 cells windowed for low or intermediate levels of fluorescence and containing cells representing approximately 20 trapped genes and analysis of the effects of these compounds on fluorescence from as many as 6,000 cells per microtitre well.

In another embodiment, an assay is provided in which approximately 875,000 chemical compound interactions with specific genes were assessed through the application of approximately 2,000 chemical compounds, in groups of 10, to microtitre wells containing pools of approximately 5,000–10,000 cells windowed for low or intermediate levels of fluorescence and containing cells representing approximately 500 trapped genes and analysis of the effects of these compounds on fluorescence from as many as 6,000 cells per microtitre well.

DESCRIPTION OF THE INVENTION

DEFINITIONS:

The term "Polynucleotide" as used herein means a polymeric form of nucleotides of at least 10 bases in length, either ribonucleotides or deoxyribonucleotides or a modified form of either type of nucleotide. The term includes single or double stranded form of DNA.

The term "Reporter Protein" or "reporter" is used interchangeably with "marker protein" or "marker" and as used herein means a protein produced from the transcription of a sequence of DNA present in the gene trap vector and which is detectable by an assay that does not depend on the endogenous gene's coding sequence that drives expression from the reporter protein.

The term "fluorescent reporter protein" or fluorescence reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins are GFP and EGFP whose presence in cells can be detected by flow cytometry methods.

The term "Trapped Gene" as used herein means a polynucleotide sequence in the genome of a cell which encodes for a protein and into which a polynucleotide sequence encoding the reporter/marker protein has been introduced.

The term "Vector" as used herein means a replicon, such as plasmid, phage or cosmid, to which another DNA segment may be attached so as to bring about the replication of the attached segment. A "vector" may further be defined as a replicable nucleic acid construct, e.g., plasmid or viral nucleic acid.

The term "Gene-Trap Vector" as used herein means a vector (such as plasmid) containing sequences allowing expression of a reporter gene from an endogenous gene's promoter when integrated into the endogenous gene. The vector may additionally contain sequence elements permitting splicing, termination of translation of the endogenous gene, internal ribosome entry, termination fo transcription, insulator sequence elements, initiation of transcription, growth of cells in selective media, sequence specific recombination, or other elements.

The term "Residence Time" as used herein means the time a particle or cell is completely illuminated by a laser beam as it flows by it in the flow cytometer. The residence time is inversely related to the cell stream velocity during FACS analysis.

The term "Florescence distribution pattern" as used herein means a pattern of specific fluorescence properties as a function of additional properties as defined by FACS analysis and which may include fluorescence and forward scatter, fluorescence and side scatter, fluorescence in one defined channel and fluorescence in a second defined channel or combinations thereof.

The present invention provides a method which can potentially screen a large number of compounds for effects on the expression of the majority, 10,000 to 30,000, of the genes expressed within a cell. Specifically, gene-trap technologies are utilized to individually mark a majority of the genes expressed within human cell lines with a reporter protein such as the enhanced green fluorescent protein (EGFP). Initial screens by high throughput automated fluorescent cell sorting technologies identify and isolate cells in which specific genes responding to individual compounds are marked (trapped). The marked genes are identified and correlated with specific compound. Thus this invention provides genetically marked cell lines suitable for high-throughput screening and linked specific lead compounds which can be characterized for their effects on the repertoire of genes expressed within the cell.

The present invention provides a method to reduce the number of cells that are required to report the effect of a chemical compound on a specifically marked gene to the minimum required for statistically reliable identifications. In one embodiment, this number is reduced to approximately 10. Assessing the minimum number of cell allows the effects of chemical compounds to be determined with increased efficiency.

The present method also provides a method to purify cells expressing genes within a specific range of expression to a level sufficient to allow sensitive measurement of changes in gene expression. Biological effects of this magnitude are desirable where the objective is modulation of intracellular signaling pathways using chemical compounds as either bioprobes or as drug development leads.

The present invention uses the "gene-trap" technology (e.g. Skarnes et al., 1992, Genes Dev; Pruitt, 1992, Development). This technology enables screening of a large number of genes and potentially the entire genome, as opposed to investigating one gene at a time. The method involves trapping genes within a genome with a fluorescent reporter, identifying and sorting cells based on the level of expression of the trapped genes as determined by FACS, expanding sorted cells to obtain desired number of cell copies containing a trapped gene, exposing the sorted and expanded cells to a plurality of compounds, identifying groups of cells in which the expression of the trapped gene is altered, identifying the chemical compound(s) producing the effect and correlating it with trapped gene. An overview of the steps required in the present invention is shown in FIG. 1. In summary, gene trap cellular libraries are constructed (panel 1), cells are sorted to pools of specific levels of fluorescence (panel 2), chemical compounds are applied (panel 3), and individual wells are interrogated for changes in level of fluorescence of a sub-set of cells (panel 4).

For trapping genes in the present invention, a polynucleotide encoding a protein having a indicator activity, preferably a fluorescent activity (termed herein as a fluorescent reporter protein) is used. For example, the green fluorescence protein gene (GFP), isolated from the jellyfish Aequorea victoria, has become available as a reporter (maker) in prokaryotes and eukaryotes. The gfp gene encodes a protein which fluoresces when excited by violet or blue-green light. Variants of GFP are also available. One such variant is the enhanced GFP or EGFP (which is shown in FIG. 1 as an example). The polynucleotide encoding EGFP is randomly integrated into the genome of the target cell. Integration events into regions of the genome encoding functional genes are selected utilizing standard selection sites such as the neomycin resistance gene and based on the requirement for an endogenous polyadenylation signal 3' to the site of integration. Expression from the reporter gene is dependent on the endogenous gene promoter into which it is integrated and reflects the level of expression from this gene, providing a rapid vital cell marker by which expression from each trapped gene can be monitored.

Gene-trap vectors useful for the present invention are already known in the art. A variety of gene trap designs may be used for the present invention. The design should be such as to ensure that expression of the reporter protein will depend upon integration of the polynucleotide encoding it within protein-coding genes. Typically, useful gene-trap vectors for the present invention will have a polynucleotide sequence encoding the fluorescent protein and is flanked by a splice acceptor site at the 5' end and a polyadenylation signal at the 3' end. Such vectors are activated following insertion into introns of the target gene. Suitable gene-trap vectors for the present invention include those disclosed in U.S. Pat. Nos. 5,922,601, 6,248,934 and 6,306,600, the disclosures of which are incorporated herein by reference.

Each cell carrying an endogenous gene marked by incorporation of the polynucleotide encoding the reporter fluorescent protein is capable of reporting the ability of chemical compounds to affect pathways required for expression from the endogenously marked gene as a change in fluorescence. This property makes it possible to assess the effect of a chemical compound on multiple genes simultaneously since populations of cells in which different endogenous genes are marked can be scored. One method by which this can be accomplished in an automated format appropriate for high-throughput analysis is by FACS. Thus, a fluorescence activated cell sorting (FACS) is used to detect cells that express the fluorescent reporter and therefore identify the tagged gene. For a general overview of the FACS, see: Herzenberg et al., (Flow Cytometry, 1976, Sci. Amer. 234:108); Flow Cytometry and Sorting, (Eds., Malamad, Mullaney and Mendelsohn, John Wiley and Sons, Inc., New York, 1979). Briefly, fluorescence activated cell sorters take a suspension of cells and pass them single file into the light path of a laser placed near a detector. The laser usually has a set wavelength. The detector measures the fluorescent emission intensity of each cell as it passes through the instrument and generates a histogram plot of cell number versus fluorescent intensity. Gates (windows) or limits can be placed on the histogram thus identifying a particular population of cells. As described herein, modifications of standard FACS techniques, based on unexpected findings, were made to increase the reliability of the technique.

FACS has the additional advantage of allowing the simultaneous isolation of responding cells. The application of FACS to the present method is illustrated in FIG. 1, panels 2–4. The marked cell population is initially sorted into pools of cells that fall within discrete windows based on fluorescence. The distribution of cells between windows is scored. This distribution is then used to determine the number of pools from each window that will need to be assessed in subsequent steps. Pools of a suitable number of cells (such as about 500) are amplified and a portion may be frozen as a permanent reference. Each pool represents the selected number (such as 500) of target genes for use in chemical compound screens.

Three methodologies were used by which fluorescent cells can be sorted to specific windows of fluorescence with increased accuracy, stability, and sensitivity to allow multiplex screen of pools of gene trap cell lines. The three methods address: 1) heterogeneity in the detection of fluorescence within a given cell during high-speed sorting that leads to inaccuracy in the initial determination of fluorescence resulting in a phenomenon termed "fluorescence heterogeneity detection" (FHD); 2) heterogeneity in the fluorescence detectable as a function of cell cycling during the assay period leading to a phenomenon termed "cell-cycle dependent reporter heterogeneity" (CDRH); 3) cellular autofluorescence that restricts the lower limit of sensitivity of fluorescence based assays. These problems effectively prevent the possibility of small volume, single pass, assays for the effects of chemical compounds on reporter gene expression or the isolation of cells from such assays that reflect marked genes responding to the chemical compound. The present assay contemplates a high throughput multiplex assay based, in part, on effective methods to solve problems associated with the FHD and CDRH phenomena. The CDRH phenomenon is common to all reporter genes and not limited to fluorescence based assays. Additional sensitivity in the detection of genes expressed at lower levels is provided by methods to mitigate cellular auto-fluorescence.

Following FACS analysis, the cell population is sorted out into convenient window sizes for plating of cells and screening of test compounds. The screen itself is performed in a micro-titer format although any format allowing repeated analysis of small volumes can be applied. In any format, a selected number of cells from a given pool are exposed to a plurality of test compounds. For example, in one embodiment, approximately 5,000 cells (representing 500 trapped genes with 10 copies of each cell representing a trapped gene) are exposed to mixtures of approximately 10 different chemicals. FACS technology is then again employed to assess the effects of compounds on individual wells where a "hit" is scored as deviation in fluorescence from the initial window by a minimal number of cells (such as approximately 10) within the well. Responding cells are sorted to separate micro-titer wells in the absence of drug since, in the case of non-cytotoxic compounds, it will be possible to recover them directly. (Cells from wells containing irreversible cytotoxic compounds will also be recoverable from previously frozen aliquots.) The net result of this screen in this example is that a single micro-titer plate containing 96 wells with 10 different compounds per well allows the effect of approximately 960 different compounds on the expression of 500 different genes to be assessed.

The present method can be used to screen chemical libraries that are generated in the laboratory by those skilled in the art or available from many other sources. Some examples of sources for chemical libraries are as follows.

One example is the NCI small molecule sample collection that has been screened in the NCI panel of 60 human tumor cell lines. Utilization of this resource will provide a broad collection of compounds with demonstrated anti tumor effects in cell culture. Many libraries of compounds have also become commercially available in recent years. Databases of these libraries can first be filtered to remove chemically reactive, exceedingly expensive, highly toxic, or otherwise unsuitable compounds. The remaining library can be filtered to remove compounds that would be unlikely to penetrate cell membranes, or be unsuitable for in vivo use, based upon certain criteria such as their CLogP, number and pKa of ionic functionalities, number of hydrogen bond donors and acceptors, and molecular weight (e.g. by applying the commonly used "Lipinski Rule of 5"). Candidate custom synthesis libraries can then be evaluated using the present invention.

Once cells are identified in which the trapped gene is found to respond to a particular chemical, standard molecular biology techniques can be used to identify the gene. Techniques such as inverse PCR or RACE can be used for this purpose and are well known to those skilled in the art.

The PCR based techniques take advantage of the known portion of the fusion transcript sequence (Frohman et al., 1988, Proc. Natl. Acad. Sci., USA., 1988:8998–9002). Typically, such sequence is be encoded by the foreign exon containing the selectable marker/reporter. The first step in the process generates single stranded complementary DNA which is used in a PCR amplification reaction. The RNA substrate for cDNA synthesis may either be total cellular RNA or an mRNA fraction, preferably the latter. mRNA is isolated from cells lysed and mRNA is bound by the complementary binding of the polyadenylate tail to a solid matrix-bound polythymidine. The bound mRNA is washed several times and the reagents of the reverse transcription (RT) reaction are added. cDNA synthesis in the RT reaction is initiated at random positions along the message by the binding of a random sequence primer (RS). This RS primer has 6–9 random nucleotides at the 3' end to bind sites in the mRNA to prime cDNA synthesis, and a 5' tail sequence of known composition to act an anchor for PCR amplification in the next step. There is therefore no specificity for the trapped message in the RT step. Alternatively, a poly-dT primer appended to the specific sequences for the PCR may be used. Synthesis of the first strand of the cDNA would then initiate at the end of each trapped gene.

In the next step, PCR amplification is used. The primers for this reaction are complementary to the anchor sequence of the RS primer and to the selectable marker. Double stranded fragments between a fixed point in the selectable marker gene and various points downstream in the appended transcript sequence are amplified. These fragments subsequently become substrates for DNA sequencing reactions.

The present invention will be further understood by the examples presented below, which are to be construed as illustrative and are not intended to be restrictive in any way.

EXAMPLE 1

This embodiment describes the establishment of gene trap cellular libraries. Gene trap cellular libraries were constructed in Jurkat cells, P19 EC cells or SF 268 glioma cells. Several vectors known in the art may be used for the present invention. Examples of useful gene-trap vectors are disclosed in U.S. Pat. Nos. 6,248,934, 6,080,576; 6,136,566; 5,922,601. The vectors used for these libraries incorporate known features of gene trap vectors where the general structure includes from 5' to 3' a splice acceptor, a triplet translational termination sequence which will terminate translation in all three reading frames from an endogenous protein, an internal ribosome entry site, the reporter gene (such as EGFP), a polyadenylation signal, an insulator sequence derived from the β-globin gene, the PGK promoter, the neomycin resistance gene and a splice donor. A vector constructed as above was used in the present invention. A second vector in which the sequence elements described above were incorporated between the inverted terminal repeats of adenoassociated virus was also constructed. In the case of the P19 EC cell gene trap library the first vector was introduced as linearized molecules by electroporation.

Electroporation was performed using a BioRad Gene Pulser II se to 200 volts and 500 µF where $1 \times 10^7$ cells were electorporated in a 1 ml volume containing between 40 and 60 µg of DNA. Cells were grown in the presence of G418 for a period of 10 days and surviving colonies were pooled. The number of colonies was approximately 1,500. Colonies were trypsinized using routine tissue culture methods and pooled to a tissue culture flask for additional culture. Cells were amplified by trypsinization and passage to additional culture flasks, retaining all of the resulting cells, until approximately $5 \times 10^7$ cells were obtained. This population was then prepared for FACS by trypsinizing and filtering using standard protocols. When cells in which the gene-trap vector has been used to trap genes, are processed as described in Example 1, and subjected to FACS analysis, fluorescence distribution patterns (such as in panel 2 of FIG. 1) are generated. Thus, cells are evaluated by cytometry to determine the presence of the specific desired population of interest. FIG. 1 is an example showing cells expressing green fluorescent protein from an EGFP containing vector integrated into the genome.

The cells are then sorted based on the level of fluorescence. The sorted cells are then distributed into one or more pools, wherein each pool represents more than one trapped gene. In a preferred embodiment, the number of sorted cells from at least one group is about 500. The cells in each pool are then expanded in culture such that a sufficient number of cells representing each trapped gene are produced to permit distinction of the effect of a test compound on the expression of the trapped gene over a control. The expanded cells are then placed into individual wells and incubated in the absence or presence of a plurality of test compounds to generate control wells and test wells respectively. The plurality of test compounds can be added to the same wells well or separate wells. After a suitable period of incubation with the test compounds, FACS analysis is conducted on the test wells and control wells to generate fluorescence distribution patterns for the cells in the test wells and control wells. A comparison of the fluorescence distribution patterns of each test well with the control well permits identification of test wells containing compounds which have altered the expression of the trapped gene. The trapped gene can then be cloned and sequenced by standard known techniques.

EXAMPLE 2

This embodiment describes a process to mitigate Fluorescence Heterogeneity Detection. This process is designed to provide pure populations of cells that express fluorescent protein derived from a transfected gene. This process includes but is not limited to flow and image cytometers. The process applies to any genomic or proteomic derived fluorescent marker expressed by any specific population of cells.

Figures 2A, 2B, 2C, 2D:
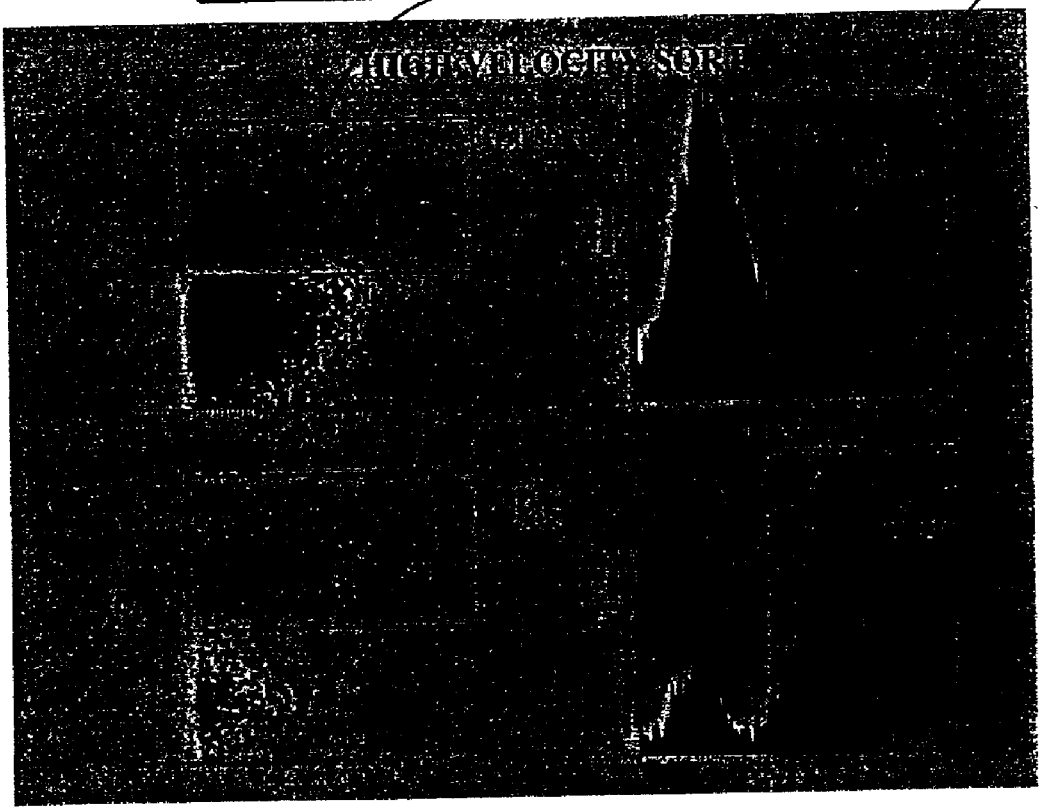
In FIG. 2B, cell number is plotted against the fluorescence.
FIGS. 2C and 2D are plots of fluorescence versus forward scatter and cell number versus fluorescence for cells sorted in window W in FIGS. 2A and 2B. Reanalysis of sorted cells indicate some improvement in GFP fluorescence, but greater than 25% fall outside the desired sort region.

Once the cells' marker characteristics have been selected, i.e. the fluorescence levels alone or as a function of other parameters as described below, the conditions of sorting are defined and the cells are sorted into appropriate collection vessels. FIG. 2 (upper panel; A and B) shows an example of cells sorted using conventional high-speed sorting on a FACS-Vantage flow sorter using a cell stream velocity of 25 meters/sec and reevaluation of the sorted cells in the lower panel (C and D). FIGS. 2A and 2B show a pattern of sorted cells (from window W) cells on the first run and FIGS. 2C and 2D show the pattern of cells on the second run. A comparison of FIGS. 2B and 2D indicates that the conventional process does not produce reproducible results since in FIG. 2D cells are clearly present outside the sort parameters selected in FIG. 2A. Thus, the conventional approach that is currently used in the art is ineffective in accomplishing the goal of providing sufficiently purified cells.

Figures 3A, 3B:
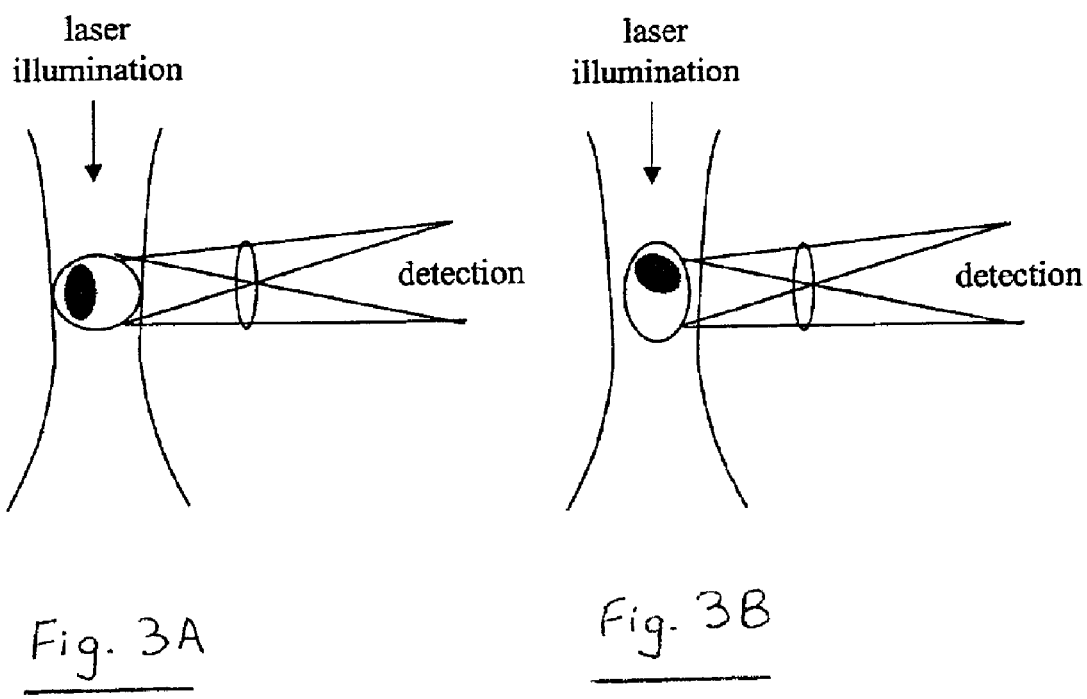
FIGS. 3A and 3B is a schematic representation of the illumination and detection of fluorescent signal in cells by FACS detection showing heterogeneity in the detection of fluorescence between A and B due to a different presentation of the fluorescent cell to the detector.

The following successful process was developed to mitigate this problem. As shown in FIGS. 3A and 3B, the excitation laser beam is 90° from the fluorescence emission detection. The current detection angle for a conventional cytometer is $\pi/6$. As a result the maximum detectable fluorescence is 4%. This can be increased by improved detection methods, for example, near $4\pi$ detectors, but this is not routinely done. This introduces the importance of the spatial distribution of cells and their fluorescence in the detection volume. Because the cells have varying degrees of opacity to photons, non-uniform fluorescence will produce non-uniform detection. Thus, the same cells that may be oriented to appear bright on one pass and meet the sorting criteria may appear dim on their second pass (or vice versa) when the sorted cells are reanalyzed, thereby causing undesired events to contaminate the desired cells and losing desired cells. This phenomenon has not been previously recognized and is referred to herein as Fluorescence Detection Heterogeneity.

A process to account for the FHD phenomenon and obtain accurate fluorescence windowing requires uniform illumination and detection. In the present invention two process are provided for reducing FHD.

One is by requiring near $4\pi$ detection. This would result in illumination and detection of cells in near $4\pi$ which is expected to resolve the problems associated with FHD detection and lead to increased speed and sensitivity.

Figure 4A:
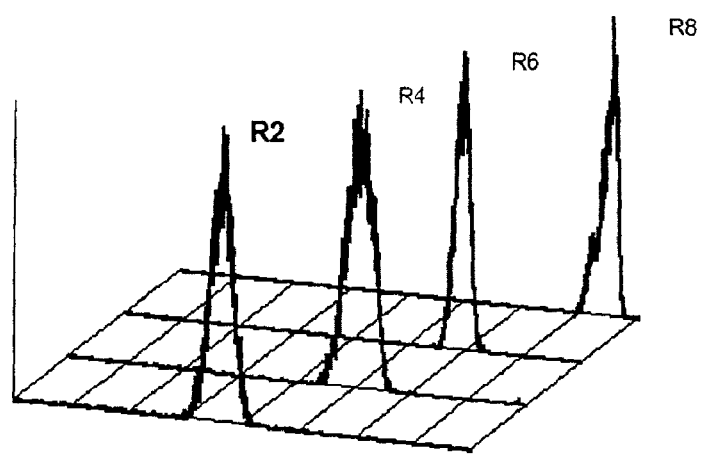
FIG. 4 shows EGFP cellular fluorescence after low speed sorting. Cells were sorted using a cell stream velocity of approximately 5 meters per second in a detection height of 30 microns. Reanalysis of sorted cells indicate a major improvement in purity of the desired cells. The initial cell population is the same as is shown in FIG. 2. In this case four discrete sorting regions are shown in FIG. 4A and termed R2, R4, R6, and R8 as a histogram of the distribution of fluorescence from individual cells. The lower panels i.e.
FIGS. 4B, 4C, 4D and 4E show dot plots of fluorescence for sorted regions R2, R4, R6 and R8 respectively as a function of forward scatter. With few exceptions, the level of contamination of sorting windows separated from the initial sort window by two or more windows is less than 0.02%. Further, in many of the exceptional cases the contaminants show a forward scatter value of less than 200 indicating that they are cellular debris, not whole cells.
Figures 4B, 4C, 4D, 4E:
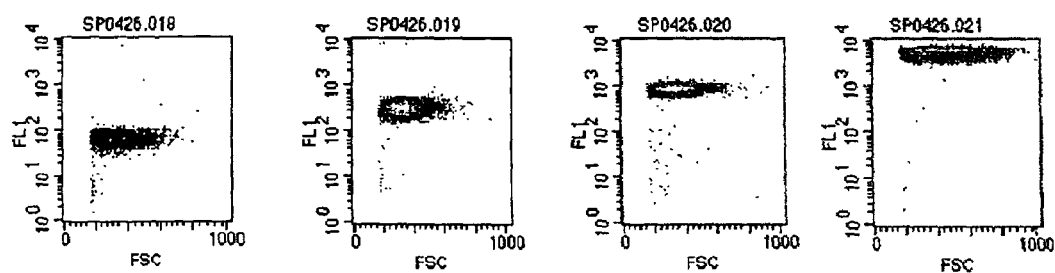

The second process involves increasing the accuracy of detection of fluorescence in individual cells by requiring the cell to rotate in an increased residence time in the detection volume. The residence time of each cell is increased by reducing the cell stream velocity to less than 25 meters per sec to a velocity wherein a beneficial effect is achieved with respect to accuracy of fluorescence determination. In a preferred embodiment, the cell stream velocity is less than about 20 meters per sec. In a more preferred embodiment, the cell stream velocity is less than about 10 meters per sec and in a still more preferred embodiment, the cell stream velocity is about 5 meters per sec. To illustrate this approach, cells were prepared and evaluated by a cytometer as described above for the conventional method except that the residence time of cells in the detection volume of the flow cytometer was increased (by reducing the cell stream velocity to 5 meters per sec) to allow it sufficient time for cell rotation. The results are shown in FIG. 4. The consequence of increasing the residence time is increased uniformity of illumination and fluorescence detection. Thus as shown in FIG. 4 this process has significantly improved the purity of the sorted population after reevaluation.

EXAMPLE 3

Figures 5A, 5B:
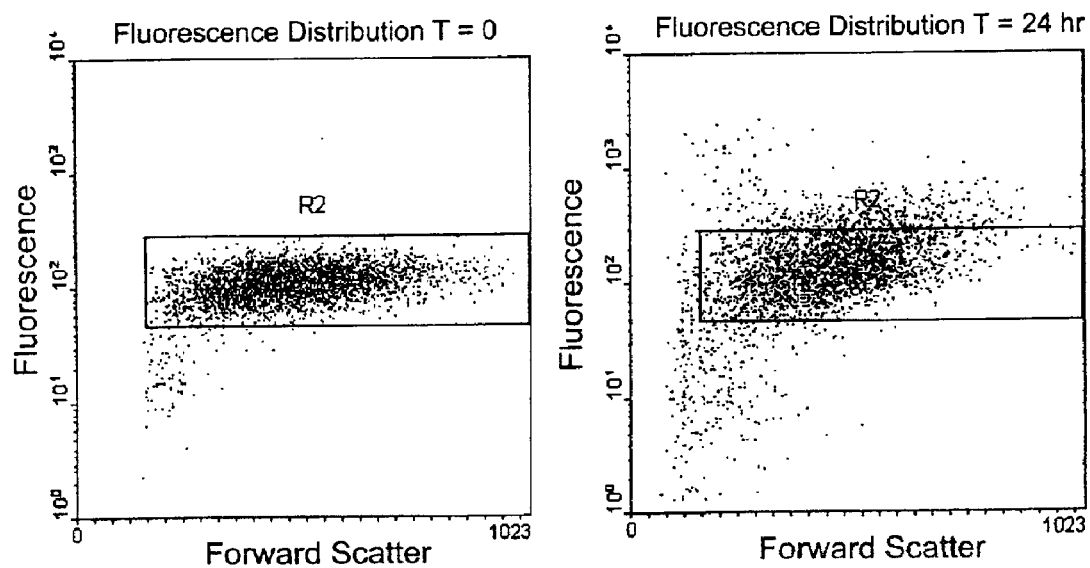
FIG. 5. Cell-cycle Dependent Reporter Heterogeneity. Cells expressing EGFP were sorted into a fluorescence windows and reassessed for purity (panel A) Following 18 hours of growth, cells were reassessed for fluorescence intensity (panels B). This figure shows that the range of intensities has spread from the initial sort windows.

This embodiment describes a method to mitigate Cell-cycle Dependent Reporter Heterogeneity. Although the process described in Example 2 produces tightly windowed populations of cells as demonstrated by re-analysis within a few hours of the original sorting, we have discovered that within 18 hours of additional growth, significant heterogeneity reoccurred in the windowed populations when using the methodologies described above. This clearly would pose a problem for evaluation of test compounds. This phenomenon is documented as shown in FIG. 5. The left panel (FIG. 5A) shows a tightly windowed population of cells shortly after sorting. The same cells are reassessed after growth in culture for 24 hours at which time their fluorescent properties have become heterogeneous relative to the initial analysis shown on the left (FIG. 5B). The basis of this heterogeneity was unexpectedly determined to be a function of the progression of cells through the cell cycle leading to the recognition of the phenomena termed herein as Cell-cycle Dependent Reporter Heterogeneity (CDRH). The consequence of this phenomena is that within a short period, generally shorter than that required for assessing the effects of a chemical compound on the expression of a reporter marked gene, cells that are initially accurately windowed to within a given range of fluorescence become heterogeneous in their fluorescence. The consequence of this phenomena is that even accurately fluorescence windowed cells may not serve as suitable target for reporting the effects of chemical compounds on gene expression in a single round assay. One solution to this problem that has been used previously is to perform multiple rounds of enrichment of cells that change gene expression. However, this approach requires larger numbers of cells and severely limits the number of assays that can be performed. Hence, even accurately fluorescence windowed cells are not suitable as a target for reporting the effects of chemical compounds on gene expression in a single round assay. This has previously prevented contemplation of the multiplexed assay that is described in the present patent.

To reduce the problems resulting from CDRH when using pools of gene trap cells in a compound screen, methods by which fluorescence (or other reporter gene measurements) can be corrected based on cell cycle parameters are contemplated here. One specific solution that is illustrated here takes advantage of the relationship between cell cycle, cell size and the ability of the forward-scattering of light in the FACS to provide a measure of cell size. Also included within the scope of this methodology is the use of alternative measurements of cell-cycle parameters, use of an internal-reference gene (e.g. a different color fluorescence tagged gene), or cell synchronization. The advantage of use of the forward scatter parameter for this purpose is its simplicity and the fact that this measurement is currently made routinely on all flow cytometers and sorters. Such methodologies are expected to have advantages for use with cell scanners or other reporter detection methods.

Figure 6A:
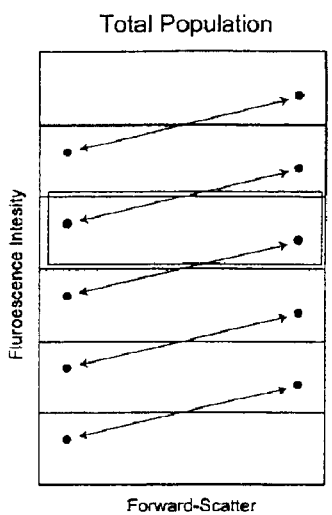
FIGS. 6A, 6B and 6C show the consequence of using standard sorting parameters, which do not correct for changes in detection of reporter gene expression with FSC during cell cycling. In this case, following the initial sort and as cells cycle into different phases of the cell cycle (indicated by arrows) their fluorescence values change causing an apparent change in their fluorescence. The consequence of this is shown in the right panel (FIG. 6C) where cells initially sorted to a discrete window of fluorescence now appear in additional windows. The lower portion of the figure (FIGS. 6D, 6E and 6F) shows the consequence of correcting for changes in detection of reporter gene expression as a function of FSC during the cell cycle. Using this correction, cells initially sorted to a specific window of fluorescence remain within the initial sort window following cycling to different phases of the cell cycle.
Figure 6B:
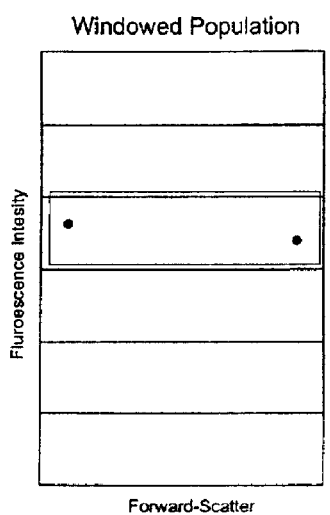
Figure 6C:
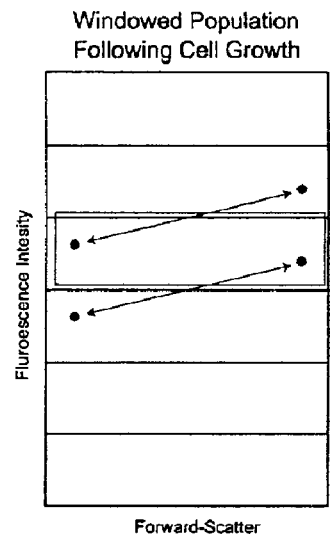

Advantage can be taken of the forward scatter parameter to normalize the fluorescent signal detected from individual cells for their position in the cell cycle as illustrated in FIGS. 6A–E. As cells cycle they change in size from relatively small during the early G1 phase shortly after division to relatively large in the late G2 phase just prior to division. During growth of the cell, and for expression from all reporter trapped genes, there is an accumulation of fluorescent protein within the cell that occurs as a function of time. At cell division this number of fluorescent proteins is halved. Additionally, changes occur in the expression of most genes during the cell cycle where expression is minimal during chromosome condensation at M-phase, accentuating the difference in fluorescence between small cells shortly after division and large cells shortly prior to division. Hence, during the cell cycle the emission of fluorescent signal from an individual cell will traverse a range of greater than two-fold. Further, this range in fluorescence will show the relationship to the forward-scatter parameter as shown in FIG. 6B. The consequence of this shift for cells that are windowed with a specific level of fluorescence that does account for the CDRH are shown in the top panel (FIGS. 6A–C). Immediately following sorting, the cells are tightly windowed. However, in an unsynchronized population, progression through the cell cycle leads to apparent heterogeneity in the signals. This heterogeneity restricts the utility of cells sorted by conventional methods for compound screening assays.

Figure 6D:
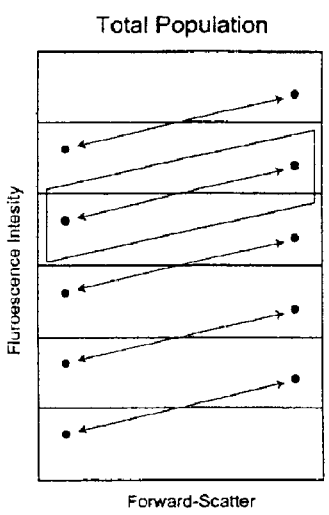
FIG. 6. is a schematic illustration of the relationship between fluorescence and forward scatter during cell cycling.
Figure 6E:
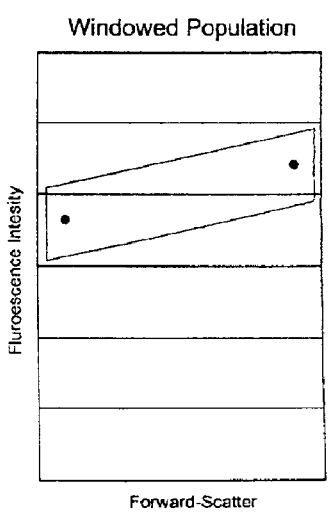
Figure 6F:
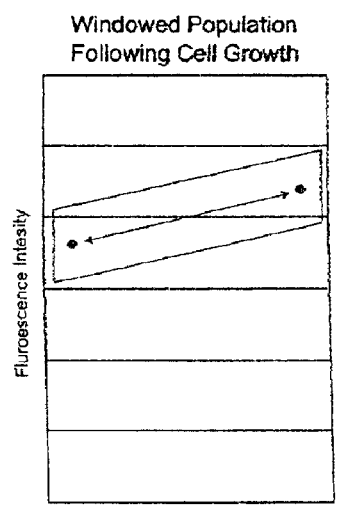
Figure 7A:
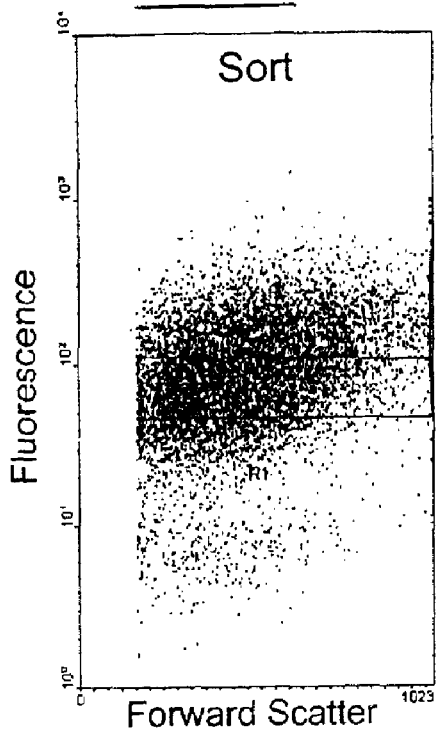
FIG. 7 illustrates the effect of compensating for CDRH in the forward scatter axis on the recovery of fluorescence windowed cells following cell growth. Cells exhibiting a range of fluorescence values were sorted based on the use of a horizontal (upper left panel, A) or slanted (lower left panel, C) sorting window in the fluorescence x forward scatter channels. Cells were allowed to grow for approximately 24 hours and reassessed using the same windows (upper right panel (B); horizontal window; lower right panel (D) slanted window).
Figure 7B:
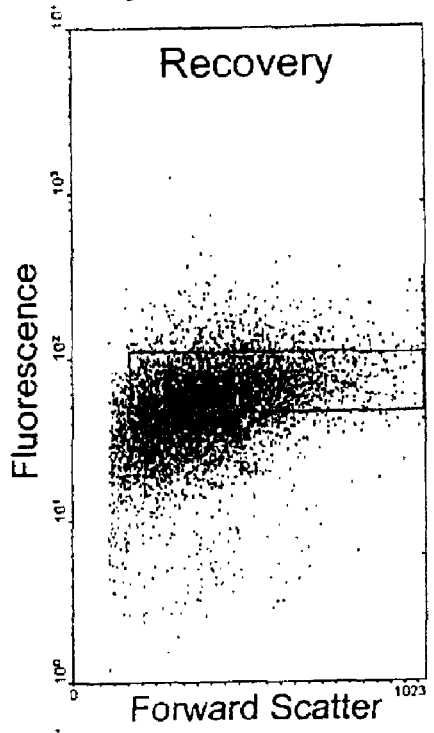
Figure 7C:
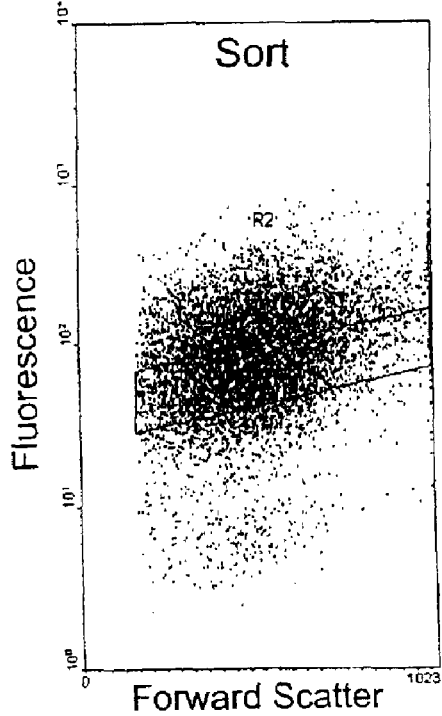
Figure 7D:
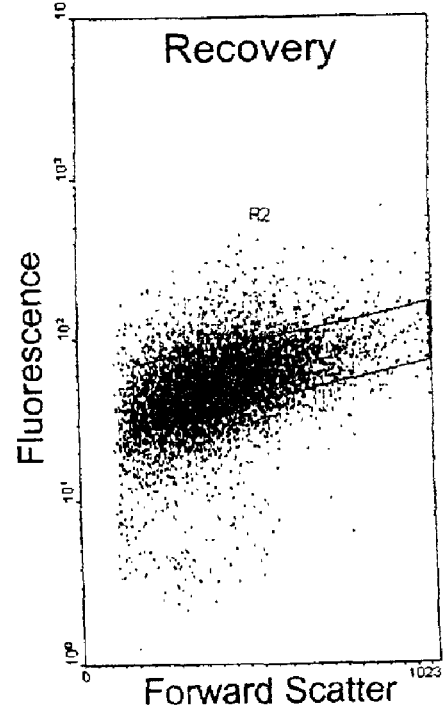

The present invention provides a method to compensate for the heterogeneity resulting from CDRH. Specifically cells are sorted using windows that account for CDRH as shown in the lower portion of FIG. 6 (FIGS. 6D–6F). Under these sorting parameters, as cells traverse the cell cycle they remain within the initial sort window and the apparent heterogeneity is eliminated.

An embodiment of this process is shown in FIG. 7 (A–D) where cells exhibiting a range of fluorescent signals were sorted using either a horizontal window, which does not account for CDRH or a slanted window, which takes CDRH into consideration. The initial sorting window was selected such that approximately 43% of the total starting population was present in either the horizontal or slanted window. Cells were sorted one time in the absence of additional methods to improve the sort such that any effect could be attributed to the change in sorting windows. Sorted cells where placed into culture for a period of approximately 18 hours and re-evaluated for the proportion present in the original sorting window. In the case of the horizontal window the percentage of cells actually decreased from 43% (FIG. 7A) to 41% (FIG. 7B). In contrast the percentage of cells recovered in the original slanted window increased from 43% (FIG. 7C) to 54% (FIG. 7D). This initial experiment demonstrates the utility of CDRH compensation in the absence of any additional techniques for improving sorting efficiency.

The effect of cell cycling on the fluorescence distribution pattern of cells can be determined empirically by following a cell, a clone of cells or group of cells as they go through cell cycle and determining their fluorescence and forward scatter parameters or other parameters that reflect cell cycling properties. Thus, both the shape and the slant of the windows for grouping of cells can be determined by empirical methods. Further examples that embody the use of CDRH compensation on more tightly windowed populations of cells are presented in Example 4 below.

EXAMPLE 4

This embodiment describes a flow cytometric process to reduce cellular auto-fluorescence and extend the useful range of fluorescence detection. Trapped genes expressed at low levels will give correspondingly low levels of fluorescent signal from a fluorescent protein reporter. At these low levels of fluorescence, cellular auto-fluorescence can obscure the useful signal range. In the present application, this has the effect of preventing analysis of the effects of chemical compounds on gene expression. To address this problem a process is provided by which much of the cellular auto-fluorescence can be reduced without affecting the level of fluorescence from the fluorescent protein. This process is applicable to reduce auto-fluorescence relative to fluorescent protein expression for any purpose.

The basis of the process is the unexpected observation that cellular auto-fluorescence is rapidly quenched by broad spectrum visible light (termed herein as white light) generally produced by incandescent light source while expression from fluorescent protein reporters is much less affected by such exposure. To apply this observation to FACS, cells are exposed immediately prior to FACS to a light source that preferentially quenches auto-fluorescence over fluorescence from the fluorescent protein reporter. In the present embodiment this is accomplished by placing a high-intensity fiber optic incandescent light source in the fluidics stream of the FACS.

Figure 8:
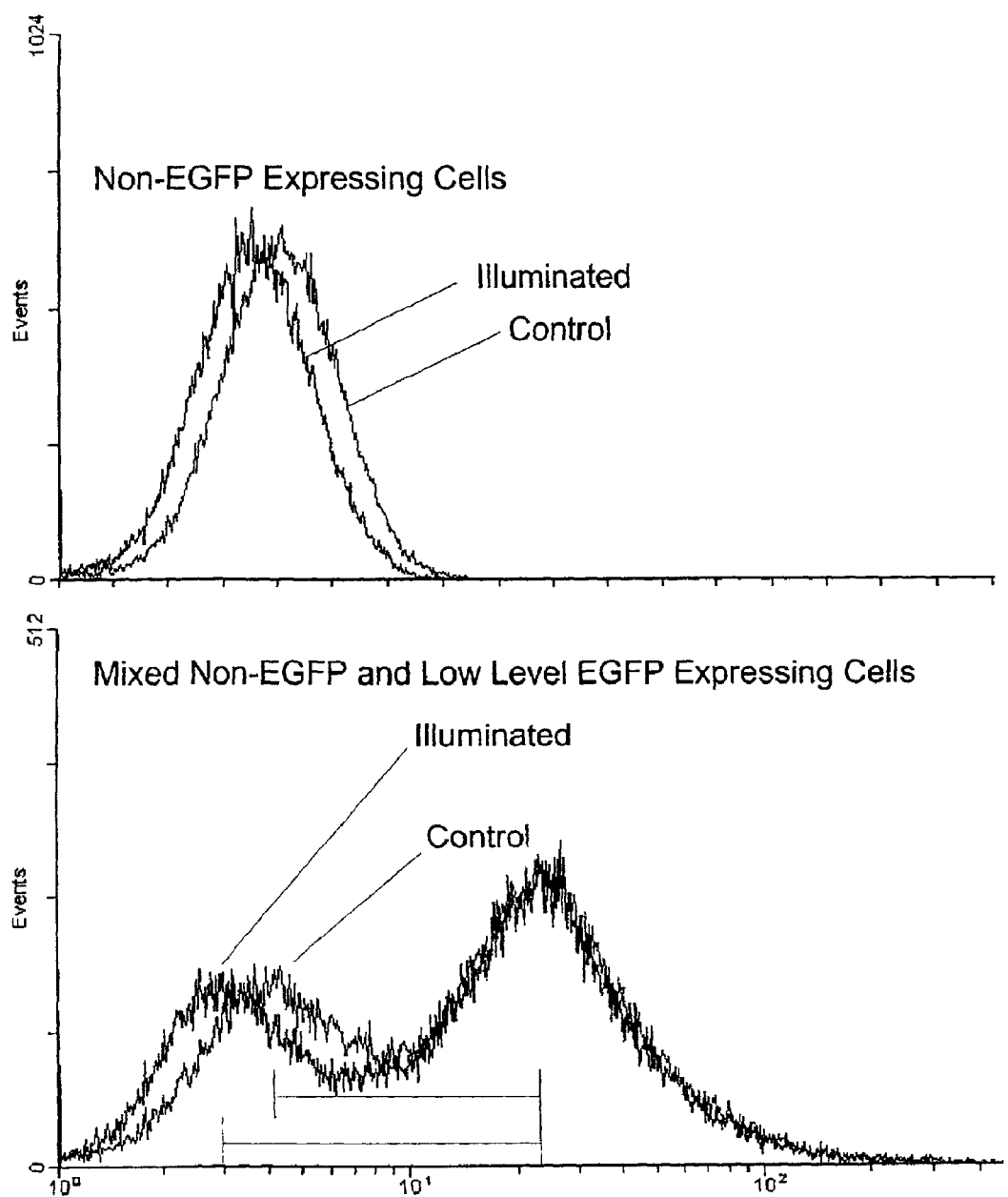
FIG. 8 is an illustration of the effect of broad spectrum illumination on auto-fluorescence and EGFP dependent fluorescence. The upper panel shows the effect of illumination on a population of control cells which do not express EGFP, all of the cells shift downwards in their fluorescence values. The lower panel shows the effect of illumination on a mixed population of cells consisting of those that do not express EGFP and those that express low levels of EGFP. In this case only the non-expressing cells show a downward shift in their fluorescence values. The consequence of this shift is a greater separation between cells with EGFP dependent fluorescence and those without as indicated by the bars.

An embodiment of the process is shown in FIG. 8. In this embodiment, two population of cells are analyzed by FACS, one does not carry a fluorescent reporter protein (upper panel) and the other (lower panel) is a mixture of low level EGFP expressing cells, resulting from gene trapping, that includes a sub-population that does not express the reporter. In each case cells were assessed without light exposure and with light exposure and histograms representing the distribution of fluorescence are overlaid. In the case of cells that do not carry the fluorescent protein reporter (upper panel), the entire population of cells is shifted to a lower level of fluorescence demonstrating a decrease in cellular auto-fluorescence. In contrast, in the population of cells containing both cells exhibiting low-level fluorescence from the fluorescent protein and non-expressing cells (lower panel), only the non-expressing cells show a downward shift in fluorescence. Hence, use of this process effectively extends the lower limit over which the fluorescent reporter protein can be detected.

EXAMPLE 5

This embodiment illustrates multiplex chemical compound screening of the present invention. Two embodiments of multiplex compound screening are presented herein. In this example, cells windowed to a mid-level of fluorescence were examined for compounds capable of either enhancing or decreasing the level of fluorescence and in Example 6, cells windowed to a low level of fluorescence are examined for compounds capable of enhancing expression.

Chemical Compounds.

In each of the screens the chemical compounds tested were the National Cancer Institutes Diversity set and the Challenge sets. The diversity set has of approximately 2,000 compounds that are selected on the basis of having a large representation of different possible structures. The challenge set consists of a set of 54 compounds that have known anti-tumor activity but for which no mechanism of action is currently known. Compounds were pooled to sets of approximately 10 and resulting in 208 pools. Of the resulting pools, 200 were used in the experiments described in this example and all 208 were used in the experiments described in Example 6.

Fluorescence Windowing of a Cellular Gene Trap Library.

The P19 EC cell cellular library described in Example 1 was prepared for screening by first establishing the range of fluorescence (fluorescence distribution pattern) exhibited from the trapped reporter genes. Based on this analysis two regions of fluorescence were selected, one representing moderately fluorescent cells and consisting of 1.4% of the total population of 1,500. Assuming that each cell represented an independent integration event this would mean approximately 20 independent integration events, and the second representing very low and non-expressing cells and consisting of 34% of the total population, or approximately 510 independent integration events.

A Low Complexity Multiplex Screen for Compounds Exhibiting Either Enhancing or Suppressing Activity on Reporter Gene Expression.

Figure 9:
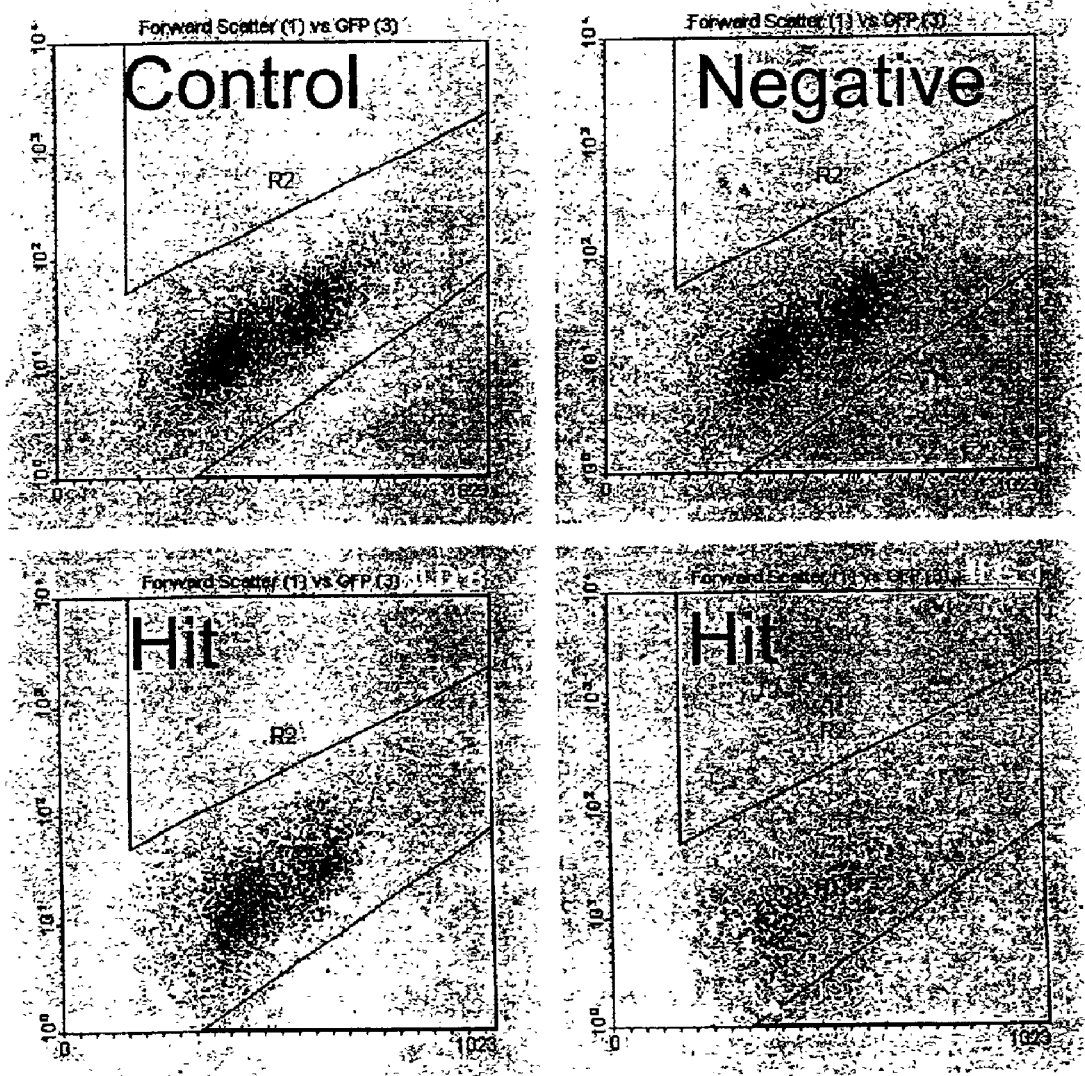
FIG. 9. A low complexity multiplex screen for compounds exhibiting either enhancing or suppressing activity on reporter gene expression showing a well with no effect of test compounds (labeled "Negative"), and two wells where reporter gene expression is altered (labeled "Hit").
Figure 10:
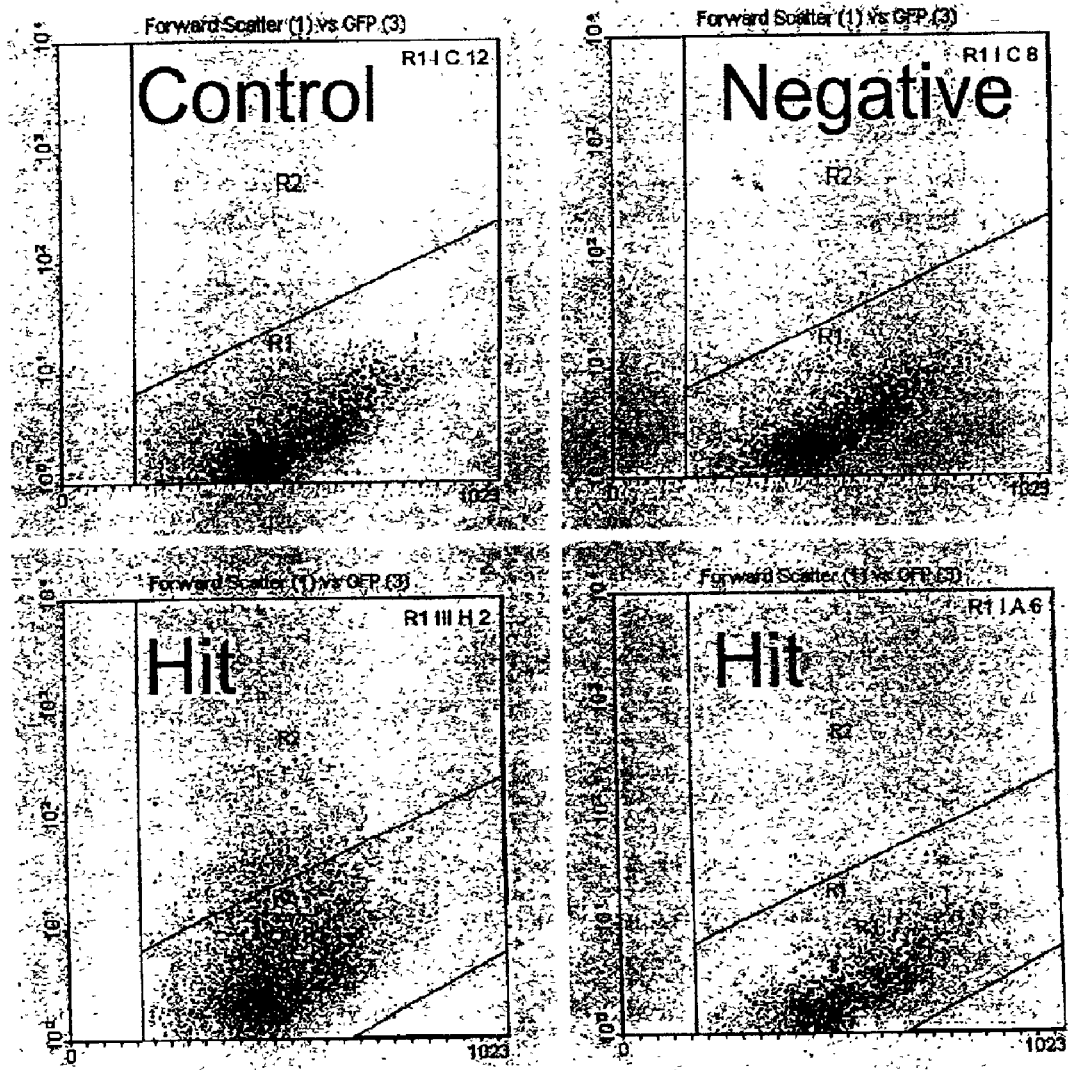
FIG. 10. A high complexity multiplex screen for compounds exhibiting either enhancing or suppressing activity on reporter gene expression showing one well with no effect of test compound (labeled "Negative") and two wells where reporter gene expression is altered (labeled "Hit").

Moderate level expressing cells were windowed using the processes described in Examples 2–4 above and approximately 5,000–10,000 cells were seeded to each of 208 microtitre wells in 200 µl of tissue culture media. Pools of chemical compounds at a final concentration of 1 µM for each compound in the case of the diversity set and 10 µM in the case of the challenge set were added in 2 ul of DMSO as a carrier to 200 of the wells. The remaining 8 wells were treated with 2 ul of DMSO carrier alone as a control. Cells were incubated for a period of approximately 40 hours at which time the tissue culture media was removed from each well and cells were prepared for fluorescence scanning by trypsinization. Cells were scanned and scored for cells exhibiting fluorescence intensities at levels that were either above or below the initial sort window. Results for one well of control cells, one negative well and 2 wells in which cells deviating from the initial fluorescence values are shown in FIG. 9. Out of a total of 208, 59 wells contained 1 or more cytotoxic compounds that prevented assessment. The 2 positive wells shown were the only wells showing deviation from the normal distribution of fluorescent cells and are considered positive for the presence of one or more compounds affecting the fluorescence from a subset of cells in this assay. The total number of chemical compounds assessed for an effect on a target gene in this low complexity multiplex assay was approximately 1,490 (in 149 readable wells)×approximately 20 target genes per well=29,800. The total transfectants in the original library can be readily increased to reach the preferred complexity of 500 target genes.

EXAMPLE 6

This embodiment demonstrates that the present invention can be used for multiplex screening of compounds to identify compounds exhibiting enhancing activity on reporter gene expression. Low level expressing cells were windowed using the processes described in Examples 2–4 above and approximately 5,000 cells were seeded to each of 216 microtitre wells in 200 µl of tissue culture media. Pools of chemical compounds at a final concentration of 1 µM or 10 µM as described above in Example 5 for each compound were added in 2 ul of DMSO as a carrier to 208 of the wells. The remaining 8 wells were treated with 2 ul of DMSO carrier alone as a control. Cells were incubated for a period of approximately 24 hours at which time the tissue culture media was removed from each well and cells were prepared for fluorescence scanning by trypsinization. Cells were scanned and scored for cells exhibiting fluorescence intensities at levels that were above the initial sort window. Results for one well of control cells, one negative well and 2 wells in which cells deviating from the initial fluorescence values are shown in figure. Fourteen wells were obtained which showed deviation from the normal distribution of fluorescent cells leading to reduced or elevated (or both) fluorescent signal in a subset of the cells and are considered positive for the presence of one or more compounds affecting the fluorescence from a subset of cells in this assay. The total number of chemical compounds assessed for an effect on a target gene in this high complexity multiplex assay was approximately 1,750 compounds (in 175 readable wells)× approximately 500 target genes per well=875,000.

The present invention as described herein permits multiplex screening of test compounds for an effect on the expression of trapped genes. Various examples have been presented above to illustrate this invention. However, minor modifications to this invention will be appreciated by those skilled in the art and are intended to be included within the scope of the invention.

What is claimed is:

1. A method of screening a plurality of test compounds to identify the presence of one or more compounds that affect expression of at least one trapped gene comprising the steps of:
   a) providing a gene-trap vector encoding a fluorescent reporter protein, wherein the fluorescent reporter protein directly or indirectly produces fluorescence;
   b) stably transfecting a population of cells with the gene-trap vector, wherein expression of the reporter protein is indicative of the expression of the trapped gene;
   c) sorting the population of stably transfected cells by FACS into groups according to expressed levels of reporter protein;
   d) distributing cells from each group into one or more pools, wherein each pool represents more than one trapped gene;
   e) expanding the cells from each pool, wherein the expansion is such that a sufficient number of cells representing each trapped gene are produced to permit distinction of the effect of a test compound on the expression of the trapped gene over a control;
   f) placing the expanded cells into individual wells;
   g) incubating the wells from each pool in the absence or presence of a plurality of test compounds to generate control wells and test wells respectively, wherein the plurality of test compounds are added to the same wells or separate wells;
   h) conducting FACS analysis on the test wells and control wells to generate fluorescence distribution patterns for the cells in the test wells and control wells;
   i) comparing the fluorescence distribution patterns of each test well with the control well; and
   j) identifying the test well in which the fluorescence distribution pattern differs from the control well, wherein identification of a different fluorescence distribution pattern is indicative of a test compound affecting the expression of one or more trapped gene represented in the test well, wherein FACS parameters are adjusted to compensate for heterogeneity in the reporter protein fluorescence due to cell cycling and wherein the cell stream velocity during FACS analysis is less than 25 meters per second, and wherein cellular auto-fluorescence is reduced by illuminating white light on the population of stably transfected cells of step c) during sorting.

2. The method of claim 1, wherein the reporter protein is the green fluorescent protein.

3. The method of claim 1, wherein the reporter protein is the enhanced green fluorescent protein.

4. The method of claim 1, wherein the number of cells in each group represents about 500 trapped genes.

5. The method of claim 1, wherein the cells from each pool are expanded at least five fold.

6. The method of claim 5, wherein the cells from each pool are expanded at least ten fold.

7. The method of claim 1, further comprising the step of cloning and sequencing the trapped gene.

8. The method of claim 1, wherein the cell stream velocity is less than 15 meters per second.

9. The method of claim 8, wherein the cell stream velocity is about 5 meters per second.

10. A method of identifying multiple modulators of a known trapped gene comprising the steps of:
    a) obtaining a clone of stably transfected cells in which the known gene has been trapped by a gene-trap vector encoding a fluorescent reporter protein has been inserted, wherein the fluorescent reporter protein directly or indirectly produces fluorescence;
    b) placing cells from the clone into multiple wells;
    c) incubating the wells in the absence or presence of a plurality of test compounds to generate control wells and test wells respectively, wherein the plurality of test compounds are added to the same wells or separate wells;
    d) conducting FACS analysis on the test wells and control wells to generate fluorescence distribution patterns for the cells in the test wells and control wells;
    e) comparing the fluorescence distribution patterns of each test well with the control well; and f) identifying the test wells in which the fluorescence distribution pattern differs from the control well, wherein identification of a different fluorescence distribution pattern is indicative of a test compound affecting the expression of the trapped gene, wherein FACS parameters are adjusted to compensate for heterogeneity in the reporter protein fluorescence due to cell cycling and wherein the cell stream velocity during FACS analysis is less than 25 meters per second, and wherein cellular auto-fluorescence is reduced by illuminating white light on the cells of step c) during sorting.

11. The method of claim 10, wherein the reporter protein is the green fluorescent protein.

12. The method of claim 10, wherein the reporter protein is the enhanced green fluorescent protein.

13. The method of claim 10, wherein the number of cells in each group represents about 500 trapped genes.

14. The method of claim 10, wherein the cells from each pool are expanded at least five fold.

15. The method of claim 14, wherein the cells from each pool are expanded at least ten fold.

16. The method of claim 10, wherein the cell stream velocity is less than 15 meters per second.

17. The method of claim 10, wherein the cell stream velocity is about 5 meters per second.

* * * * *

UNITED STATES PATENT AND TRADEMARK OFFICE
CERTIFICATE OF CORRECTION

PATENT NO.       : 7,083,919 B2  
APPLICATION NO.  : 10/139420  
DATED            : August 1, 2006  
INVENTOR(S)      : Pruitt et al.

It is certified that error appears in the above-identified patent and that said Letters Patent is hereby corrected as shown below:

Title page, item (73), the assignee should read:
--Health Research, Inc., Buffalo, NY (US);
The Research Foundation of State University of New York, Amherst, NY (US)--.

Signed and Sealed this

Twelfth Day of June, 2007

JON W. DUDAS
*Director of the United States Patent and Trademark Office*